United States Patent
Ranade et al.

(10) Patent No.: US 9,993,403 B2
(45) Date of Patent: Jun. 12, 2018

(54) COSMETIC COMPOSITIONS FOR IMPARTING SUPERHYDROPHOBIC FILMS

(75) Inventors: Rahul A. Ranade, Emerson, NJ (US); John R. Glynn, Jr., Ridgewood, NJ (US); Mark S. Garrison, Suffern, NY (US); Shari Martin, Suffern, NY (US); Prithwiraj Maitra, Randolph, NJ (US)

(73) Assignee: AVON PRODUCTS, INC., Rye, NY (US)

( * ) Notice: Subject to any disclaimer, the term of this patent is extended or adjusted under 35 U.S.C. 154(b) by 637 days.

(21) Appl. No.: 12/747,430

(22) PCT Filed: Nov. 14, 2008

(86) PCT No.: PCT/US2008/083498
§ 371 (c)(1),
(2), (4) Date: Jun. 10, 2010

(87) PCT Pub. No.: WO2009/082565
PCT Pub. Date: Jul. 2, 2009

(65) Prior Publication Data
US 2010/0266648 A1    Oct. 21, 2010

Related U.S. Application Data

(60) Provisional application No. 61/015,355, filed on Dec. 20, 2007.

(51) Int. Cl.
| | |
|---|---|
| *A61K 8/02* | (2006.01) |
| *A61K 8/25* | (2006.01) |
| *A61K 8/06* | (2006.01) |
| *A61K 8/11* | (2006.01) |
| *A61K 8/29* | (2006.01) |
| *A61K 8/895* | (2006.01) |
| *A61K 8/898* | (2006.01) |
| *A61Q 1/02* | (2006.01) |
| *A61Q 1/10* | (2006.01) |
| *A61Q 5/00* | (2006.01) |
| *A61Q 17/04* | (2006.01) |
| *A61Q 19/00* | (2006.01) |

(52) U.S. Cl.
CPC ............ *A61K 8/25* (2013.01); *A61K 8/06* (2013.01); *A61K 8/064* (2013.01); *A61K 8/11* (2013.01); *A61K 8/29* (2013.01); *A61K 8/895* (2013.01); *A61K 8/898* (2013.01); *A61Q 1/02* (2013.01); *A61Q 1/10* (2013.01); *A61Q 5/00* (2013.01); *A61Q 17/04* (2013.01); *A61Q 19/00* (2013.01); *A61K 2800/413* (2013.01)

(58) Field of Classification Search
CPC . A61K 8/25; A61K 8/06; A61K 8/064; A61K 8/11; A61K 8/21; A61K 8/895; A61K 8/898; A61K 2800/413; A61Q 1/02; A61Q 1/10; A61Q 5/00; A61Q 17/04; A61Q 19/00
See application file for complete search history.

(56) References Cited

U.S. PATENT DOCUMENTS

| | | |
|---|---|---|
| 2,705,206 A | 3/1955 | Wagner et al. |
| 3,393,155 A | 7/1968 | Schutte et al. |
| 4,049,007 A | 9/1977 | Russell et al. |
| 4,122,029 A | 10/1978 | Gee et al. |
| 4,614,200 A | 9/1986 | Hsiong et al. |
| 4,781,917 A | 11/1988 | Luebbe et al. |
| 5,000,937 A | 3/1991 | Grollier et al. |
| 5,362,486 A | 11/1994 | Nandagiri et al. |
| 5,500,216 A | 3/1996 | Julian et al. |
| 5,665,368 A * | 9/1997 | Lentini et al. ............... 424/401 |
| 5,688,831 A | 11/1997 | El-Nokaly et al. |
| 5,911,980 A | 6/1999 | Samour et al. |
| 5,948,393 A | 9/1999 | Tomomasa et al. |
| 6,132,739 A | 10/2000 | Leverett |
| 6,159,486 A | 12/2000 | Terren et al. |
| 6,228,927 B1 * | 5/2001 | Lucarelli et al. ............. 524/493 |
| 6,248,336 B1 | 6/2001 | McDermott |
| 6,264,933 B1 | 7/2001 | Bodelin et al. |
| 6,315,990 B1 | 11/2001 | Farer et al. |
| 6,464,969 B2 | 10/2002 | De la Poterie et al. |
| 6,534,044 B1 | 3/2003 | Wada et al. |
| 6,683,126 B2 | 1/2004 | Keller et al. |
| 6,685,952 B1 | 2/2004 | Ma et al. |
| 6,709,648 B2 | 3/2004 | Sako et al. |
| 6,800,354 B2 | 10/2004 | Baumann et al. |
| 6,852,389 B2 | 2/2005 | Nun et al. |
| 6,946,170 B2 | 9/2005 | Gerber et al. |
| 7,037,515 B2 | 5/2006 | Kalafsky et al. |
| 7,056,845 B2 | 6/2006 | Waeber et al. |
| 7,083,828 B2 | 8/2006 | Muller et al. |
| 7,150,878 B2 | 12/2006 | Gonzalez et al. |
| 2003/0235553 A1 * | 12/2003 | Lu et al. ................. 424/70.122 |
| 2004/0009130 A1 | 1/2004 | Donna et al. |
| 2004/0028709 A1 | 2/2004 | Dueva et al. |
| 2004/0033451 A1 | 2/2004 | Fujita et al. |
| 2005/0180936 A1 | 8/2005 | Pays |
| 2005/0201961 A1 * | 9/2005 | Lu et al. ......................... 424/63 |
| 2006/0110541 A1 | 5/2006 | Russell et al. |

(Continued)

FOREIGN PATENT DOCUMENTS

| | | |
|---|---|---|
| JP | 63-072616 A2 | 4/1988 |
| JP | 01-139521 A2 | 6/1989 |

(Continued)

OTHER PUBLICATIONS

Anonymous. Silicas and Aluminas. Cabot Corporation [online]; downloaded from URL<http://www.cabot-corp.com/silicas-and-aluminas> on Jun. 12, 2014; 2 pages.*

(Continued)

*Primary Examiner* — David Browe
(74) *Attorney, Agent, or Firm* — Brian P. McCloskey; Elizabeth Morters

(57) ABSTRACT

Compositions and methods are disclosed for imparting super-hydrophobic properties to cosmetics, which can be used to significantly improve water repellency compared to traditional cosmetics. The compositions comprise a hydrophobic film former, and hydrophobic particles, in an emulsion base.

14 Claims, 1 Drawing Sheet

(56) References Cited

U.S. PATENT DOCUMENTS

| | | |
|---|---|---|
| 2006/0110542 A1 | 5/2006 | Dietz et al. |
| 2007/0020208 A1 | 1/2007 | Gutkowski |
| 2007/0044248 A1 | 3/2007 | Bratescu |
| 2008/0085254 A1 | 4/2008 | Nguyen et al. |
| 2008/0226575 A1 | 9/2008 | Hanna |

FOREIGN PATENT DOCUMENTS

| | | | | |
|---|---|---|---|---|
| JP | 07-215829 A | | 8/1995 | |
| JP | 08-269332 A2 | | 10/1996 | |
| JP | H09-124444 A2 | | 5/1997 | |
| JP | H11-100306 A2 | | 4/1999 | |
| JP | H11-100307 A2 | | 4/1999 | |
| JP | 2000-072622 A2 | | 3/2000 | |
| JP | 2000-327528 | | 11/2000 | |
| JP | 2000-327533 | | 11/2000 | |
| JP | 2001-181136 A2 | | 7/2001 | |
| JP | 2001181136 | * | 7/2001 | ............... A61K 8/18 |
| JP | 2002-039921 A2 | | 1/2002 | |
| JP | 2004-107673 A2 | | 4/2004 | |
| JP | 2007-182406 A2 | | 7/2007 | |
| JP | 2007-238690 A2 | | 9/2007 | |
| JP | 2007-269642 A2 | | 10/2007 | |
| WO | 2005/039520 A1 | | 5/2005 | |
| WO | 2005/063903 A1 | | 7/2005 | |
| WO | 200704517 A1 | | 4/2007 | |
| WO | 2009111128 A1 | | 11/2009 | |

OTHER PUBLICATIONS

McKay, Tonya, et al. 2005. All about another hard-to-pronounce compound. Naturally Curly.com [online]; downloaded from URL<http://www.naturallycurly.com/curlreading/curl-products/all-about-another-hard-to-pronounce-ingredient/> on Jun. 12, 2014; 10 pages.*

Cayton RH, et al. 2005. The Impact of Nano-Materials on Coating Technologies. NSTI_Nanotech [online]; downloaded from <URL: www.nsti.org/publications/Nanotech/2005/pdf/829.pdf> on Jan. 22, 2015; 3 pages.*

U.S. Appl. No. 12/920,506, filed Sep. 1, 2010, Ranade, Rahul A. et al.

* cited by examiner

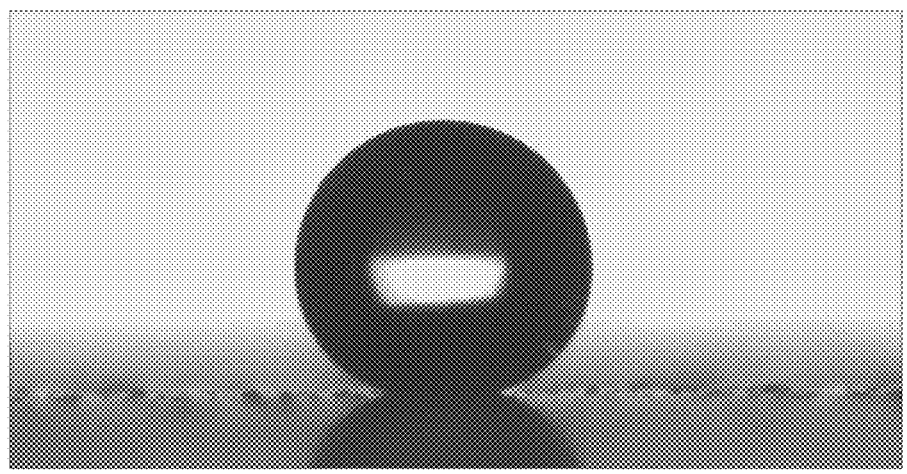

COSMETIC COMPOSITIONS FOR IMPARTING SUPERHYDROPHOBIC FILMS

RELATED APPLICATIONS

This application claims priority to International Application Serial No. PCT/US08/83498 filed Nov. 14, 2008, which claims priority U.S. Provisional Patent Application Ser. No. 61/015,355, filed Dec. 20, 2007, the contents of which are hereby incorporated by reference in their entirety.

FIELD OF INVENTION

The present invention relates to methods and compositions for imparting a film on a surface. More specifically, the invention relates to cosmetic compositions and methods for forming a super-hydrophobic film on the skin or hair.

BACKGROUND OF THE INVENTION

The leaf of the lotus plant exhibits remarkable water-repellency and self-cleaning properties. Although lotus plants prefer to grow in muddy rivers and lakes, the leaves and flowers remain clean and are essentially non-wettable. The lotus plant achieves this effect by producing leaves and flowers with extremely hydrophobic surfaces. When the leaves come in contact with water, the water droplets contract into substantially spherical beads which roll off the surface, sweeping away any particles of dirt they encounter.

On extremely hydrophilic surfaces, a water droplet will completely spread and provide an effective contact angle of essentially 0°. This occurs for surfaces that have a large affinity for water, including materials that absorb water. On many hydrophilic surfaces, water droplets will exhibit contact angles of about 10° to about 30°. In contrast, on hydrophobic surfaces, which are incompatible with water, larger contact angles are observed, typically in the range of about 70° to about 90° and above. Some very hydrophobic materials, for example, Teflon™, which is widely regarded as a benchmark of hydrophobic surfaces, provides a contact angle with water of as high as 120°-130°.

Against this background, it is remarkable that the lotus leaf can produce a contact angle with water of about 160°, which is substantially more hydrophobic that Teflon™. The lotus leaf is thus an example of a "super-hydrophobic" surface. For the present purposes, a super-hydrophobic surface may be said to be one which provides a contact angle with water of greater than about 140°. This effect is believed to arise due to the three-dimensional surface structure of the leaf wherein wax crystals self-organize to provide roughness on a nano- or micro-meter scale. The hydrophobic surface protuberances reduce the effective surface contact area with water and thus prevent adhesion and spreading of the water over the leaf.

The discovery of the aforementioned properties of the lotus leaf and elucidation of its mechanism has led to a variety of engineered super-hydrophobic surfaces. Such super-hydrophobic surfaces have water contact angles ranging from 140° to nearly 180°. Such surfaces are extremely difficult to wet. On these surfaces, water droplets simply rest on the surface, without actually wetting to any significant extent. Superhydrophobic surfaces have been obtained in a variety of ways. Some of these very hydrophobic materials are found in nature. Other superhydrophobic materials are made synthetically, sometimes as mimics of natural materials.

U.S. Pat. No. 6,683,126 describes a coating composition for producing difficult to wet surfaces comprising a finely divided powder, where the particles are porous and have a hydrophobic surface, combined with a film forming binder such that the ratio of the powder to the binder is 1:4.

U.S. Pat. No. 6,852,389 describes the process of production of superhydrophobic materials for self cleaning applications.

U.S. Pat. No. 6,946,170 describes a self cleaning display device.

U.S. Pat. No. 7,056,845 describes a method for the application of a finishing layer which is water repellant for use in finishing of textiles, fabrics and tissues.

U.S. Pat. No. 6,800,354 describes process of production of self cleaning substrates of glass, ceramic, and plastics.

U.S. Pat. No. 5,500,216 describes a method of reducing drag through water by applying a film of rough particles of hydrophobic metal oxides where the particles have a distribution of two different size ranges.

While hydrophobic or super-hydrophobic materials have been described above, there remains a need for hydrophobic or super-hydrophobic materials in cosmetic compositions to impart superhydrophobic films on surfaces such as skin, hair, or nails. Conventional water-proof or water-resistant cosmetic compositions are generally made from oil-in-water or water-in-oil emulsions. Water-in-oil emulsions tend to have an oily feel, thus limiting their use. The conventional approach to formulating water-proof or water-resistant cosmetic compositions relies on the use of hydrophobic film formers (e.g. waxes) to form a water-resistant barrier. Such conventional cosmetics are at best hydrophobic, as opposed to the super-hydrophobic films of the present invention.

Conventional water-proof or water-resistant topical compositions are not super-hydrophobic primarily because they lack nano-scale or micro-scale surface roughness. In the absence of roughness on the nano- or micro-meter scale, smooth films made of currently known hydrophobic materials exhibit contact angles that are not in the super-hydrophobic range, i.e., they are less than 140°. It would be desirable to provide cosmetic films which impart super-hydrophobic films for improving water repellency, self-cleaning properties, and long-wear properties.

It is therefore an object of the invention to provide cosmetic compositions for application to the skin, hair, or nails which form a super-hydrophobic film thereon. It is a further object of the invention to provide methods for imparting superhydrophobic films to skin, hair, and nails to achieve water-resistant, self-cleaning and/or long-wear properties.

SUMMARY OF THE INVENTION

In accordance with the foregoing objectives and others, the present invention provides compositions and methods for forming super-hydrophobic films on a surface, preferably a biological integument, such as skin, nail, or hairs. The compositions of the invention are in the form of water-in-oil or water-in-silicone emulsions. That superhydrophobic films can be produced from water-containing compositions is unexpected, as water, which is by definition hydrophilic, would be expected to reduce the hydrophobicity of the surface. However, it is has surprisingly been found that water-based emulsion formulations are capable of providing superhydrophobic films if certain other constituents are maintained within critical ranges. Thus, it is possible to formulate a variety of products in emulsion form which have aesthetic and functional attributes not attainable with anhydrous-based compositions.

In one aspect of the invention, a composition is provided for imparting a hydrophobic film on a surface comprising a water-in-oil emulsion. The water-in-oil emulsion includes (i) a continuous oil-phase; (ii) a discontinuous (internal) aqueous phase; (iii) an emulsifier having an HLB value less than 10, preferably less than 8.5; (iv) one or more hydrophobic film formers, and (v) one or more hydrophobic particulate materials having a median particle size between about 5 nm and about 1 mm.

In a related aspect of the invention, a composition for imparting a hydrophobic film on a surface comprising a water-in-silicone emulsion. The water-in-silicone emulsion includes (i) a continuous silicone oil-phase; (ii) a discontinuous aqueous phase; (iii) an emulsifier comprising an organosiloxane polymer having side chains comprising -(EO)$_m$— and/or —(PO)$_n$— groups, where n and m are integers from zero to about 25 and where the sum of n and m is at least 1 but about 50 or less, the side chains being terminated with hydrogen or lower alkyl groups; (iv) one or more hydrophobic film formers, and (v) one or more hydrophobic particulate materials having a median particle size between about 5 nm and about 1 mm.

In both the water-in-oil and water-in silicone emulsions, the weight ratio of the one or more hydrophobic film formers to the one or more hydrophobic particulate materials is suitably from about 1:5 to about 5:1, with higher levels of particulate material being preferred; and the one or more hydrophobic film formers and one or more hydrophobic particulate materials collectively comprise at least about 1% by weight, preferably at least about 2% by weight, more preferably at least about 5% by weight of the water-in-oil or water-in-silicone emulsion.

To achieve the desired superhydrophobic effect, the aggregate weight percentage of all non-volatile water-soluble or water-dispersible organic constituents (i.e., non-volatile hydrophilic organic molecules) in the emulsions should be less than 15%, preferably below 5%, and ideally below 2%; and the weight percentage of all polyols, including the humectant glycerin, should be collectively below 5%, preferably below 2%, and ideally below 1% by weight, based on the entire weight of the emulsion; because such components tend to attract water and coat the surface of the film and consequently reduce the hydrophobicity thereof.

The one or more hydrophobic particulate materials typically comprise an oxide particle selected from the group consisting of silicon dioxide, titanium dioxide, aluminum oxide, zirconium dioxide, tin dioxide, zinc oxide, iron oxide and combinations thereof, the oxide particle having hydrophobic moieties such as alkyl, fluoroalkyl, perfluoroalkyl, siloxane, alkylsiloxane, fluoroalkylsiloxane, and/or perfluoroalkylsiloxane, covalently bound to the surface thereof. The preferred hydrophobic particles are surface treated fumed (pyrogenic) silica particles or surface treated fumed (pyrogenic) alumina particles, which typically have a median particle size between about 7 nm and about 40 nm.

The one or more hydrophobic film formers include any hydrophobic film former compatible with a human integument, and may, for example, be selected from the group consisting of (alkyl)acrylates, polyurethanes, fluoropolymers, silicones, and copolymers thereof. An acrylates/dimethicone copolymer is currently preferred.

The compositions are capable of providing a film on a surface which, after evaporation of volatile constituents, is characterized by a contact angle with water greater than about 140°, preferably greater than about 145°, and optimally greater than about 150°.

The emulsion may be useful for a variety of products, including cosmetic products (mascara, foundation, etc.); skin care products; sunscreens; hair care products; and pet care products, to name a few.

Methods for providing a hydrophobic film on the skin or hair are also provided. The methods generally comprise depositing on skin or hair the emulsions according to the invention and allowing the volatile constituents to evaporate, thereby forming a hydrophobic film characterized by a contact angle with a water droplet of at least 140°.

These and other aspects of the present invention will become apparent to those skilled in the art after a reading of the following detailed description of the invention, including the figures and appended claims.

BRIEF DESCRIPTION OF FIGURES

FIG. 1 is a photograph showing a water droplet resting on a glass slide on which has been deposited a super-hydrophobic film by applying thereto an emulsion according to the invention.

DETAILED DESCRIPTION

As used herein, the term "superhydrophobic" refers generally to any surface which gives a contact angle with water of greater than 140°. Superhydrophobicity can be quantitatively evaluated by measuring the contact angle with water using a contact angle goniometer or other like method known in the art or may be qualitatively evaluated by visual inspection and observation of water repellency, i.e., observation of water beads rolling off a cast film.

Superhydrophobicity provides water repellency to a surface and consequently will affect the long-wear properties and self-cleaning properties of cosmetic compositions following administration to the skin, nails, or hair. In addition, it is thought that compositions according to the invention reduce adhesivity of pollutants, dirt, and the like to skin, nails, or hair because of a mismatch in surface energy. As a result, pollutants, dirt, and the like are more easily removed with or without water, resulting in self-cleaning properties. More importantly, the compositions provide a barrier against water such that the skin or hair does not become wet or is only poorly wettable on contact with water, e.g. sweat, rain, etc.

The inventive cosmetic compositions for imparting superhydrophobic films generally comprise a water-in-oil emulsion having included therein one or more cosmetic film formers, one or more hydrophobic or hydrophobically modified particulate materials having a median particle size between about 10 nm and about 1 mm, and one or more emulsifiers. As used herein, the water-in-oil emulsions include water-in-silicone emulsion.

The compositions are preferably capable of providing a film on a surface, after evaporation of volatile solvents, which is characterized by a contact angle with a water droplet greater than about 140°, preferably greater than about 145°, and more preferred still, greater than about 150°. The contact angle is a measure of the hydrophobicity of the surface and is the angle at which a liquid/vapor interface meets a solid surface. Contact angles are suitably measured using a contact angle goniometer.

The first required component of the composition according to the invention is a film-former. The film former preferably comprises a hydrophobic material. The hydrophobic film former may be any hydrophobic film former suitable for use in a cosmetic composition including, but not limited to, hydrophobic film-forming polymers. The term film-forming polymer may be understood to indicate a polymer which is capable, by itself or in the presence of at least one auxiliary film-forming agent, of forming a continuous film which adheres to a surface and functions as a binder for the particulate material. The term "hydrophobic" film-forming polymer will typically refer to a polymer with a solubility in water at 25° C. of less than about 1% by weight or one in which the monomeric units of the polymer individually have a solubility in water of less than about 1% by weight at 25° C. Alternatively, a "hydrophobic" film forming polymer may be said to be one which partitions preponderantly into the octanol phase when shaken with a mixture of equal volumes of water and octanol. By predominately is meant more the 50% by weight, but preferably more than 75% by weight, more preferably more than 95% by weight will partition into the octanol phase.

The film formers can be either natural or synthetic, polymeric or non polymeric, resins, binders, with low or high molar mass. Polymeric film formers can be either natural or synthetic, addition or condensation, homochain or heterochain, monodispersed or polydispersed, organic or inorganic, homopolymers or copolymers, linear or branched or crosslinked, charged or uncharged, thermoplastic or thermoset, elastomeric, crystalline or amorphous or both, isotactic or syndiotactic or atactic.

Polymeric film formers include polyolefins, polyvinyls, polacrylates, polyurethanes, silicones, polyamides, polyesters, fluoropolymers, polyethers, polyacetates, polycarbonates, polyimides, rubbers, epoxies, formaldehyde resins, and homopolymers and copolymers of and of the foregoing.

Suitable hydrophobic (lipophilic) film-forming polymers include, without limitation, those described in U.S. Pat. No. 7,037,515 to Kalafsky, et al.; U.S. Pat. No. 6,685,952 to Ma et al.; U.S. Pat. No. 6,464,969 to De La Poterie, et al.; U.S. Pat. No. 6,264,933 to Bodelin, et al.; U.S. Pat. No. 6,683,126 to Keller et al.; and U.S. Pat. No. 5,911,980 to Samour, et al., the disclosures of which are hereby incorporated by reference.

Special mention may be made of polyalkylenes, and in particular $C_2$-$C_{20}$ alkene copolymers, such as polybutene; alkylcelluloses with a linear or branched, saturated or unsaturated $C_1$-$C_8$ alkyl radical, such as ethylcellulose and propylcellulose; copolymers of vinylpyrrolidone (VP) and in particular copolymers of vinylpyrrolidone and of $C_2$ to $C_{40}$ and better still $C_3$ to $C_{20}$ alkene, including the copolymers of vinyl pyrollidone with eicosene or dodecane monomers sold under the tradenames Ganex V 220 and Ganex V 216 Polymers (ISP Inc. of Wayne, N.J.); silicone polymers and polyorganosiloxanes, including without limitations, polyalkyl siloxane, polyaryl siloxane, or a polyalkylaryl siloxane, with special mention being made of polydimethylsiloxanes; polyanhydride resins such as those available from Chevron under the trade name PA-18; copolymers derived from maleic anhydride and $C_3$ to $C_{40}$ alkenes such as octadecene-1; polyurethane polymers, such as Performa V 825 (New Phase Technologies) and those disclosed in U.S. Pat. No. 7,150,878 to Gonzalez, et al., incorporated by reference herein; and polymers and copolymers made from esters of vinylic acid monomers, including without limitation (meth)acrylic acid esters (also referred to as (meth) acrylates), for example, alkyl (meth)acrylates, wherein the alkyl group is chosen from linear, branched and cyclic ($C_1$-$C_{30}$) alkyls, such as, for example, ($C_1$-$C_{20}$) alkyl (meth) acrylates, and further still ($C_6$-$C_{10}$) alkyl (meth)acrylates.

Among the alkyl (meth)acrylates which may be mentioned are those chosen from methyl methacrylate, ethyl methacrylate, butyl methacrylate, isobutyl methacrylate, 2-ethylhexyl methacrylate, lauryl methacrylate, and the like. Among the aryl (meth)acrylates which may be mentioned are those chosen from benzyl acrylates, phenyl acrylate, and the like. The alkyl group of the foregoing esters may be chosen, for example, from fluorinated and perfluorinated alkyl groups, that is to say that some or all of the hydrogen atoms of the alkyl group are replaced with fluorine atoms. Mention may also be made of amides of the acid monomers such as (meth)acrylamides, for example, N-alkyl(meth)acrylamides, such as ($C_1$-$C_{20}$) alkyls, including without limitation, N-ethylacrylamide, N-t-butylacrylamide, N-t-octylacrylamide and N-undecylacrylamide. Vinyl polymers for the hydrophobic film-forming polymer may also result from the homopolymerization or copolymerization of at least one monomer chosen from vinyl esters, olefins (including fluoroolefins), vinyl ethers, and styrene monomers. For example, these monomers may be copolymerized with at least one of acid monomers, esters thereof, and amides thereof, such as those mentioned above. Non-limiting examples of vinyl esters which may be mentioned are chosen from vinyl acetate, vinyl neodecanoate, vinyl pivalate, vinyl benzoate and vinyl t-butylbenzoate. Among the olefins which may be mentioned are those chosen, for example, from ethylene, propylene, butene, isobutene, octene, octadecene, and polyfluorinated olefins chosen, for example, from tetrafluoroethylene, vinylidene fluoride, hexafluoropropene and chlorotrifluoroethylene. Styrene monomers which may be mentioned are chosen, for example, from styrene and alpha-methylstyrene. The list of monomers given is not limiting, and it is possible to use any monomer known to those skilled in the art which falls within the categories of acrylic and vinyl monomers (including monomers modified with a silicone chain) which result in hydrophobic films. In this regard, particular mention may be made of the commercially available film formers Cyclopentasiloxane (and) Acrylates/Dimethicone Copolmer (KP-545, Shinetsu Chemical Co., Ltd).

Other film formers known in the art can be used advantageously in the composition. These include acrylate copolymers, acrylates $C_{12\text{-}22}$ alkyl methacrylate copolymer, acrylate/octylacrylamide copolymers, acrylate/VA copolymer, amodimethicone, AMP/acrylate copolymers, behenyl/isostearyl, butylated PVP, butyl ester of PVM/MA copolymers, calcium/sodium PVM/MA copolymers, dimethicone, dimethicone copolymers, dimethicone/mercaptopropyl methicone copolymer, dimethicone propylethylenediamine behenate, dimethicolnol ethylcellulose, ethylene/acrylic acid copolymer, ethylene/MA copolymer, ethylene/VA copolymer, fluoro $C_{2\text{-}8}$ alkyldimethicone, $C_{30\text{-}38}$ olefin/isopropyl maleate/MA copolymer, hydrogenated styrene/butadiene copolymer, hydroxyethyl ethylcellulose, isobutylene/MA copolymer, methyl methacrylate crosspolymer, methylacryloyl ethyl betaine/acrylates copolymer, octadecene/MA copolymer, octadecene/maleic anhydride copolymer, octylacrylamide/acrylate/butylaminoethyl methacrylate copolymer, oxidized polyethylene, perfluoropolymethylisopropyl ether, polyethylene, polymethyl methacrylate, polypropylene, PVM/MA decadiene crosspolymer, PVM/MA copolymer, PVP, PVP/decene copolymer, PVP/eicosene copolymer, PVP/hexadecene copolymer, PVP/MA copolymer, PVP/MA copolymer, sodium acrylate/vinyl alcohol copolymer, stearoxy dimethicone, stearoxytrimethylsilane, stearyl alcohol, stearylvinyl ether/MA copolymer, styrene/DVB copolymer, styrene/MA copolymer, tetramethyl tetraphenyl trisiloxane, tricontanyl PVP, trimethyl pentaphenyl trisiloxane, trimethylsiloxysilicate, VA/crotonates copolymer, VA/crotonates/vinyl proprionate copolymer, VA/butyl maleate/isobornyl acrylate copolymer, vinyl caprolactam/PVP/dimethylaminoethyl methacrylate copolymer, and vinyldimethicone.

Additional non-limiting representatives of hydrophobic film-forming polymers include at least one polycondensate chosen from polyurethanes, polyurethane-acrylics, polyurethane-polyvinylpyrrolidones, polyester-polyurethanes, polyether-polyurethanes, polyureas and polyurea/polyurethanes. The polyurethanes may be for example, at least one chosen from aliphatic, cycloaliphatic, and aromatic polyurethanes, polyurealurethanes, and polyurea copolymers comprising at least one of: at least one sequence of at least one aliphatic polyester origin, cycloaliphatic polyester origin, and aromatic polyester origin at least one branched and unbranched silicone sequence, for example, from polydimethylsiloxane and polymethylphenylsiloxane, and at least one sequence comprising fluorinated groups. Additional non-limiting representatives of polycondensates may be chosen from polyesters, polyesteramides, fatty-chain polyesters, polyamides resins, epoxyester resins, arylsulphonamide-epoxy resins, and resins resulting from the condensation of formaldehyde with an arylsulphonamide.

The hydrophobic film may also be formed in situ by employing a resin which cures after application to the skin, nails, or hair, including for example, a polydimethylsiloxane film formed by in situ hydrosilation of a hydrosilane and an olefinic-substituted siloxane or by in situ polycondensation of alkoxy-functionalized siloxanes.

Preferred polymeric film formers include acrylates, alkyl acrylates, polyurethanes, fluoropolymers such as Fluomer (polyperfluoroperhydrophenanthrene) and silicone polymers. Particularly preferred are silicone acrylates such as acrylates/dimethicone copolymers sold under the trade names KP-545 or KP 550 (Shin-Etsu).

Other film formers that may be employed include, without limitation, natural, mineral and/or synthetic waxes. Natural waxes are those of animal origin, including without limitation beeswax, spermaceti, lanolin, and shellac wax, and those of vegetable origin, including without limitation carnauba, candelilla, bayberry, and sugarcane wax, and the like. Mineral waxes contemplated to be useful include, without limitation ozokerite, ceresin, montan, paraffin, microcrystalline, petroleum, and petrolatum waxes. Synthetic waxes include, for example, Fischer Tropsch (FT) waxes and polyolefin waxes, such as ethylene homopolymers, ethylene-propylene copolymers, and ethylene-hexene copolymers. Representative ethylene homopolymer waxes are commercially available under the tradename POLYWAX® Polyethylene (Baker Hughes Incorporated). Commercially available ethylene-α-olefin copolymer waxes include those sold under the tradename PETROLITE® Copolymers (Baker Hughes Incorporated). Another wax that is suitable is dimethiconol beeswax available from Noveon as ULTRABEE™ dimethiconol ester.

In some embodiments, it may be desirable to add a hydrophilic or water-soluble film former (e.g., cellulosics, polysaccharides, polyquaterniums, etc.) to the composition to improve spreading, emulsion stability, etc. While less preferred, it is within the scope of the invention to include such hydrophilic or water-soluble film formers. There is no restriction on the amount of hydrophilic or water-soluble film former, although at high levels (e.g., greater than 20% by weight based on the total weight of film former) it may be necessary to increase the ratio of hydrophobic particulate to film former to counter the reduction in surface hydrophobicity. In some embodiments, the collective weight percentage of hydrophilic or water-soluble film formers will be less than about 20%, preferably less than about 15%, more preferably less than about 10%, and more preferred still, less than about 5% by weight based on the total weight of all film formers. In a preferred embodiment, hydrophilic film formers will comprise less than about 2% by weight of the total weight of film formers in the emulsion. In one embodiment, the emulsion is substantially free of water-soluble film formers by which is meant that the amount of water-soluble film formers present does not impart a measurable difference in contact angle with water as compared to an otherwise identical composition in the absence of water-soluble film formers.

Combinations of any of the foregoing film formers are also contemplated to be suitable, including combinations or polymeric and non-polymeric film formers.

A second essential component according to the invention is a particulate material which is either hydrophobic by nature or has been hydrophobically modified by surface treatment or the like. While not wishing to be bound by theory, it is thought that the particulate materials provide nano-scale (1 nm to ~1,000 nm) or micro-scale (1 μm to ~200 μm) surface roughness or structure on the film, which imparts superhydrophobicity by providing protuberances on which water droplets may sit, thereby minimizing contact of the water with the surface at large, i.e., reducing surface adhesion. Surface roughness can be observed or measured by AFM, SEM, and the like. In some, but not all, embodiments, the particulate materials are not porous.

A preferred particulate material according to the invention is hydrophobically modified silica ($SiO_2$) powder, including fumed silica or pyrogenic silica (e.g., having a particle size range from about 7 nm to about 40 nm). Other notable particulate materials are hydrophobically modified metal oxides, including without limitation titanium dioxide ($TiO_2$), aluminum oxide ($Al_2O_3$), zirconium dioxide ($ZrO_2$), tin dioxide ($SnO_2$), zinc oxide (ZnO), and combinations thereof.

Advantageously, the particulate material may be one which provides additional functionality to the compositions, including for example, ultraviolet (UV) light absorption or scattering, in the case of, for example, titanium dioxide and zinc oxide particulates, or provide aesthetic characteristics, such as color (e.g., pigments), pearlesence (e.g. mica), or the like. The particulate material may be based, for example, on organic or inorganic particulate pigments. Examples of organic particulate pigments include lakes, especially aluminum lakes, strontium lakes, barium lakes, and the like. Examples of the inorganic particulate pigments are iron oxide, especially red, yellow and black iron oxides, titanium dioxide, zinc oxide, potassium ferricyanide ($K_3Fe(CN)_6$), potassium ferrocyanide ($K_4Fe(CN)_6$), potassium ferrocyanide trihydrate ($K_4Fe(CN)_6.3H_2O$), and mixtures thereof. The particulate material may also be based on inorganic fillers such as talc, mica, silica, and mixtures thereof, or any of the clays disclosed in EP 1 640 419, the disclosure of which is hereby incorporated by reference.

In one embodiment, particulate materials are surface-treated to impart a hydrophobic coating thereon. Hydrophobically modified particulates and methods for preparing hydrophobically modified particulates are well-known in the art, as described in, for example, U.S. Pat. No. 3,393,155 to Schutte et al., U.S. Pat. No. 2,705,206 to Wagner et al., U.S. Pat. No. 5,500,216 to Wagner et al., U.S. Pat. No. 6,683,126 to Keller et al., and U.S. Pat. No. 7,083,828 to Müller et al., U.S. Patent Pub. No. 2006/0110541 to Russell at al., and U.S. Patent Pub. No. 2006/0110542 to Dietz et al., the disclosures of which are hereby incorporated by reference. In one embodiment, a hydrophobic particle in accordance with an embodiment of the present invention may be formed from an oxide particle (e.g., a metal oxide, silicon dioxide, etc.) having its surface covered with (e.g., covalently bonded to) non-polar radicals, such as for example alkyl groups, silicones, siloxanes, alkylsiloxanes, organosiloxanes, fluorinated siloxanes, perfluorosiloxanes, organosilanes, alkylsilanes, fluorinated silanes, perfluorinated silanes and/or disilazanes and the like. U.S. Pat. No. 6,315,990 to Farer, et al., the disclosure of which is hereby incorporated by reference, described suitable fluorosilane coated particulates which are formed by reacting a particulate having a nucleophilic groups, such as oxygen or hydroxyl, with a silicon-containing compound having a hydrocarbyl group substituted by at least one fluorine atom and a reactive hydrocarbyloxy group capable of displacement by a nucleophile. An example of such a compound is tridecafluorooctyltriethoxy silane, available from Sivento, Piscataway, N.J., under the trade name DYNASILANE™ F 8261. The hydrophobically modified silica materials described in U.S. Patent Pub. 2006/0110542 to Dietz et al., incorporated herein by reference, are contemplated to be particularly suitable.

Any of the hydrophobically modified particulate materials described in U.S. Pat. No. 6,683,126 to Keller et al., the disclosure of which is hereby incorporated by reference herein, are also contemplated to be useful, including without limitation those obtained by treating an oxide material (e.g., $SiO_2$, $TiO_2$, etc.) with a (perfluoro)alkyl-containing compound that contains at least one reactive functional group that undergoes a chemical reaction with the near-surface OH groups of the oxide support particle, including for example hexamethyldisilazane, octyltrimethoxysilane, silicone oil, chlorotrimethylsilane, and dichlorodimethylsilane.

Suitable hydrophobically modified fumed silica particles include, but are not limited to AEROSIL™ R 202, AEROSIL™ R 805, AEROSIL™ R 812, AEROSIL™ R 812 S, AEROSIL™ R 972, AEROSIL™ R 974, AEROSIL™ R 8200, AEROXIDE™ LE-1, AEROXIDE™ LE-2, and AEROXIDE™ LE-3 from Degussa Corporation of Parsippany, N.J. Other suitable particulates include the particulate silicon wax sold under the trade name Tegotop™ 105 (Degussa/Goldschmidt Chemical Corporation) and the particulate vinyl polymer sold under the name Mincor™ 300 (BASF). While silica ($SiO_2$) and hydrophobically-modified silicas are contemplated to be particularly useful in some embodiments, in other embodiments the compositions will be substantially free of silica or hydrophobically-modified silica. By substantially free of silica or hydrophobically-modified silica means that these components comprise less than about 2%, preferably less than about 1%, and more preferably less than about 0.5% by weight of the one or more particulate materials. A suitable hydrophobically modified alumina particulate is ALU C 805 from Degussa.

The one or more particulate materials may also comprise particulate organic polymers such as polytetrafluoroethylene, polyethylene, polypropylene, nylon, polyvinyl chloride, and the like which have been formed into fine powders. Alternatively, the particulate material may be a microcapsule comprising any of the shell materials described in U.S. Patent Pub. 2005/0000531, the disclosure of which is hereby incorporated by reference herein.

The one or more particulate materials will typically be in the form of a powder having a median particle size between about 1 nm (nanometers) and about 1 mm (millimeters), more typically between about 5 nm and about 500 μm (micrometer), preferably between about 7 nm and about 1 μm, 5 μm, 20 λm, 50 μm or about 100 μm. Where more than one particulate material is employed (e.g., modified $TiO_2$ and modified $SiO_2$), the median particle size of each powder is preferably within the foregoing ranges.

Particulate materials having median particle sizes above about 1 mm may be too large, unless the particle itself contains surface roughness in the appropriate size range. For example, surface treatment of a larger particle with a polymer chain in the 20 nm range may provide acceptable surface roughness. Roughness of the resulting films may be characterized by the size of the primary particle, by the size of agglomerated particles in the aggregate, or by the distribution of particle sizes.

Ratios of the individual components in the compositions according to the invention are controlled to produce compositions with the desired superhydrophobic effect. For example, the weight of hydrophobic film-former to particulate material may range from about 1:2 to about 2:1, including the ratio of about 1:2, about 1:1.75, about 1:1.5, about 1:1.25, about 1:1, about 1.25:1, about 1.5:1, about 1.75:1, and about 2:1. Particular good results have been obtained where the weight ratio of hydrophobic film-former to particulate material is about 1:1.

The hydrophobic film-former and particulate material may collectively comprise at least about 50%, at least about 60%, at least about 70% or at least about 80% by weight of the non-volatile portion of the emulsion. Typically, the hydrophobic film-former and particulate material will collectively comprise less than about 95%, less than about 90%, or less than about 85% by weight of the non-volatile portion of the emulsion. In one embodiment the hydrophobic film-former and particulate material collectively comprise about 80% (or greater than 80%) to about 90% by weight of the non-volatile portion of the emulsion.

Water-in-Oil Emulsion

The compositions according to the invention are preferably formulated as water-in-oil emulsions. These emulsions comprise an oil-containing continuous phase and an aqueous discontinuous phase.

The oil-containing phase will typically comprise from about 10% to about 99%, preferably from about 20% to about 85%, and more preferably from about 30% to about 70% by weight, based on the total weight of the emulsion, and the aqueous phase will typically comprise from about 1% to about 90%, preferably from about 5% to about 70%, and more preferably from about 20% to about 60% by weight of the total emulsion. The aqueous phase will typically comprise from about 25% to about 100%, more typically from about 50% to about 95% by weight water.

The oil-containing phase may be composed of a singular oil or mixtures of different oils. Essentially any oil is contemplated to be useful, although highly hydrophobic oils are preferred. Suitable non-limiting examples include vegetable oils; esters such as octyl palmitate, isopropyl myristate and isopropyl palmitate; ethers such as dicapryl ether; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; natural or synthetic waxes; and the like.

Suitable hydrophobic hydrocarbon oils may be saturated or unsaturated, have an aliphatic character and be straight or branched chained or contain alicyclic or aromatic rings. Hydrocarbon oils include those having 6-20 carbon atoms, more preferably 10-16 carbon atoms. Representative hydrocarbons include decane, dodecane, tetradecane, tridecane, and $C_{8-20}$ isoparaffins. Paraffinic hydrocarbons are available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename Permethyl 99A™ are also contemplated to be suitable. Various commercially available $C_{16}$ isoparaffins, such as isohexadecane (having the tradename Permethyl R™) are also suitable. Examples of preferred volatile hydrocarbons include polydecanes such as isododecane and isodecane, including for example, Permethyl-99A (Presperse Inc.) and the $C_7$-$C_8$ through $C_{12}$-$C_{15}$ isoparaffins such as the Isopar Series available from Exxon Chemicals. A representative hydrocarbon solvent is isododecane.

What is critical is that the emulsions have little or no non-volatile hydrophilic constituents, including some conventional humectants. Components such as glycerin and polyols, including propylene glycol, ethoxydiglycol, glycerin, butylene glycol, pentylene glycol and hexylene glycol should be eliminated or should be kept at levels such that the non-volatile hydrophilic constituents, in the aggregate, do not exceed 15% by weight and preferably will be less than 10%, less than 5%, less than 2%, or less than 1% by weight. Glycerin has been found to be particularly detrimental to achieving superhydrophobicity and should therefore be maintained at levels below 2% by weight, or eliminated altogether.

It has been found that the selection and amount of emulsifier is important for obtaining films which provide superior hydrophobic properties. Because the emulsifier itself may be deleterious to the formation of a superhydrophobic film, the compositions preferably have the lowest level of emulsifier capable of producing a stable emulsion. The amount of emulsifier will typically be from about 0.001 wt % to about 10 wt %, but preferably will range from about 0.01 to about 5 wt %, and most preferably about 0.1 wt % to about 1 wt %, based upon the total weight of the composition.

For water in oil emulsions, the emulsifier itself should be of low HLB, preferably below 10, more preferably below 8.5. While combinations of more than one emulsifier are contemplated to be within the scope of the invention, each such emulsifier, individually, should be of low HLB. Therefore, the use of high and low HLB emulsifiers, which in combination give low HLB (e.g., less than 8.5), is less desirable because even if the combined HLB of the system is below 8.5, the contribution of the higher HLB emulsifier will be detrimental to the formation of a superhydrophobic film. If present, the amount of emulsifier having an HLB above 10 will be less than 1% by weight, more preferably less than 0.5% by weight, and more preferred still, lees than 0.2% by weight.

Where the emulsifier is of the polyethoxylated type (e.g., polyoxyethylene ethers or esters) comprising chains of the form $-(CH_2CH_2O)_n-$, n is generally less than 20, preferably less than 10, more preferably less than 7, and most preferably less than 5. Propoxylated emulsifiers are also contemplated to be suitable. Propoxylated emulsifiers typically have less than 20, more preferably less than 10, most preferably less than 5 propylene oxide repeat units.

Emulsifiers that can be used in the composition of the present invention include, but are not limited to, one or more of the following: sorbitan esters; polyglyceryl-3-diisostearate; sorbitan monostearate, sorbitan tristearate, sorbitan sesquioleate, sorbitan monooleate; glycerol esters such as glycerol monostearate and glycerol monooleate; polyoxyethylene phenols such as polyoxyethylene octyl phenol and polyoxyethylene nonyl phenol; polyoxyethylene ethers such as polyoxyethylene cetyl ether and polyoxyethylene stearyl ether; polyoxyethylene glycol esters; polyoxyethylene sorbitan esters; dimethicone copolyols; polyglyceryl esters such as polyglyceryl-3-diisostearate; glyceryl laurate; Steareth-2, and Steareth-6, to name a few. Additional emulsifiers are provided in the INCI Ingredient Dictionary and Handbook 11th Edition 2006, the disclosure of which is hereby incorporated by reference.

An example of a very low HLB emulsifier contemplated to be suitable according to the invention is Span 83, a sequester of monooleate and dioleate at a 2:1 molar ratio which has an HLB of 3.7. Sorbitan monostearate (INCI) is another suitable emulsifier, having an HLB value of 4.7.

The aqueous phase may include one or more additional solvents, preferably volatile solvents, including lower alcohols, such as ethanol, isopropanol, and the like. The volatile solvent may also be a cosmetically acceptable ester such as butyl acetate or ethyl acetate; ketones such as acetone or ethyl methyl ketone; or the like. The volatile solvents, when present in the aqueous phase, will typically comprise from about 0.1% to about 75% by weight of the aqueous phase, more typically up to about 35% by weight, and preferably up to about 15% by weight. The water and optional volatile solvents are contemplated to enhance the formation of a superhydrophobic film because the particulates will tend to be pushed to the surface of the film as the solvents evaporate.

Water-in-Silicone Emulsion

One type of water-in-oil emulsion that has been found to be useful is a water-in-silicone emulsions having a silicone oil-containing continuous phase and an aqueous discontinuous phase.

The silicone-containing phase will typically comprise from about 20% to about 95%, preferably from about 25% to about 85%, and more preferably from about 35% to about 70 the aqueous phase will typically comprise from about 5% to about 90%, preferably from about 10% to about 70%, and more preferably from about 20% to about 60% by weight of the total emulsion. The aqueous phase will typically comprise from about 25% to about 100%, more typically from about 50% to about 95% by weight water.

The silicone oil phase may include volatile silicone oils, non-volatile silicone oils, and combinations thereof. By volatile silicone oil is meant that the oil readily evaporates at ambient temperatures. Typically, volatile silicone oils will exhibit a vapor pressure ranging from about 1 Pa to about 2 kPa at 25° C.; will preferably have a viscosity of from about 0.1 to about 10 centistokes, preferably about 5 centistokes or less, more preferably about 2 centistokes or less, at 25° C.; and will boil at atmospheric pressure at from about 35° C. to about 250° C.

Volatile silicones include cyclic and linear volatile dimethylsiloxane silicones. In one embodiment, the volatile silicones may include cyclodimethicones, including tetramer (D4), pentamer (D5), and hexamer (D6) cyclomethicones, or mixtures thereof. Particular mention may be made of the volatile cyclomethicone-hexamethyl cyclotrisiloxane, octamethyl-cyclotetrasiloxane, and decamcthyl-cyclopentasiloxane. Suitable dimethicones are available from Dow Corning under the name Dow Corning 200° Fluid and have viscosities ranging from 0.65 to 600.000 centistokes or higher. Suitable non-polar, volatile liquid silicone oils are disclosed in U.S. Pat. No. 4,781,917, herein incorporated by reference in its entirety. Additional volatile silicones materials are described in Todd et al., "Volatile Silicone Fluids for Cosmetics", Cosmetics and Toiletries, 91:27-32 (1976), herein incorporated by reference in its entirety. Linear volatile silicones generally have a viscosity of less than about 5 centistokes at 25° C. whereas the cyclic silicones have viscosities of less than about 10 centistokes at 25° C. Examples of volatile silicones of varying viscosities include Dow Corning 200, Dow Corning 244, Dow Corning 245, Dow Corning 344, and Dow Corning 345, (Dow Corning Corp.); SF-1204 and SF-1202 Silicone Fluids (G E Silicones), GE 7207 and 7158 (General Electric Co.) and SWS-03314 (SWS Silicones Coro). Linear, volatile silicones include low molecular weight polydimethylsiloxane compounds such as hexamethyldisiloxane, octamethyltrisiloxane, decamethytetrasiloxane, and dodecamethylpentasiloxane to name a few.

Non-volatile silicone oils will typically comprise polyalkylsiloxanes, polyarylsiloxanes, polyalkylarylsiloxanes, or mixtures thereof. Polydimethylsiloxanes are preferred non-volatile silicone oils. The non-volatile silicone oils will typically have a viscosity from about 10 to about 60,000 centistokes at 25° C., preferably between about 10 and about 10,000 centistokes, and more preferred still between about 10 and about 500 centistokes; and a boiling point greater than 250° C. at atmospheric pressure. Non limiting examples include dimethyl polysiloxane (dimethicone), phenyl trimethicone, and diphenyldimethicone.

The volatile and non-volatile silicone oils may optionally be substituted will various functional groups such as alkyl, aryl, amine groups, vinyl, hydroxyl, haloalkyl groups, alkylaryl groups, and acrylate groups, to name a few.

The water-in-silicone emulsion is emulsified with a non-ionic surfactant (emulsifier). Suitable emulsifiers include polydiorganosiloxane-polyoxyalkylene block copolymers, including those described in U.S. Pat. No. 4,122,029, the disclosure of which is hereby incorporated by reference. These emulsifiers generally comprise a polydiorganosiloxane backbone, typically polydimethylsiloxane, having side chains comprising -(EO)$_m$— and/or —(PO)$_n$— groups, where EO is ethyleneoxy and PO is 1,2-propyleneoxy, the side chains being typically capped or terminated with hydrogen or lower alkyl groups (e.g., C$_{1-6}$, typically C$_{1-3}$). The side chains will preferably comprise 50 EO and/or PO units or less (e.g., m+n=<50), preferably 20 or less, and more preferably 10 or less. In addition to the alkoxylated side chain, the silicone emulsifier may also comprise alkyl chains pendant from the silicone backbone. Other suitable water-in-silicone emulsifiers are disclosed in U.S. Pat. No. 6,685,952, the disclosure of which is hereby incorporated by reference herein. Commercially available water-in-silicone emulsifiers include those available from Dow Corning under the trade designations 3225C and 5225C FORMULATION AID; SILICONE SF-1528 available from General Electric; ABIL EM 90 and EM 97, available from Goldschmidt Chemical Corporation (Hopewell, Va.); and the SILWETT™ series of emulsifiers sold by OSI Specialties (Danbury, Conn.).

Examples of water-in-silicone emulsifiers include, but are not limited to, dimethicone PEG10/15 crosspolymer, dimethicone copolyol, cetyl dimethicone copolyol, PEG-15 lauryl dimethicone crosspolymer, laurylmethicone crosspolymer, cyclomethicone and dimethicone copolyol, dimethicone copolyol (and) caprylic/capric triglycerides, polyglyceryl-4 isostearate (and) cetyl dimethicone copolyol (and) hexyl laurate, and dimethicone copolyol (and) cyclopentasiloxane.

Preferred examples of water-in-silicone emulsifiers include, without limitation, PEG/PPG-18/18 dimethicone (trade name 5225C, Dow Corning), PEG/PPG-19/19 dimethicone (trade name BY25-337, Dow Corning), Cetyl PEG/PPG-10/1 dimethicone (trade name Abil EM-90, Goldschmidt Chemical Corporation), PEG-12 dimethicone (trade name SF 1288, General Electric), lauryl PEG/PPG-18/18 methicone (trade name 5200 FORMULATION AID, Dow Corning), PEG-12 dimethicone crosspolymer (trade name 9010 and 9011 silicone elastomer blend, Dow Corning), PEG-10 dimethicone crosspolymer (trade name KSG-20, Shin-Etsu), and dimethicone PEG-10/15 crosspolymer (trade name KSG-210, Shin-Etsu).

The water-in-silicone emulsifiers typically will be present in the composition in an amount from about 0.001% to about 10% by weight, in particular in an amount from about 0.01% to about 5% by weight, and more preferably, below 1% by weight.

Various fillers and additional components may be added. Suitable fillers include without limitation silica, treated silica, talc, zinc stearate, mica, kaolin, Nylon powders such as Orgasol™, polyethylene powder, Teflon™, starch, boron nitride, copolymer microspheres such as Expancel™ (Nobel Industries), Polytrap™ (Dow Corning) and silicone resin microbeads (Tospearl™ from Toshiba), and the like.

Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; organic powder such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide; and stabilizers/rheology modifiers, for example, Bentone Gel and Rheopearl TT2. Other useful powders are disclosed in U.S. Pat. No. 5,688,831, the disclosure of which is hereby incorporated by reference.

The compositions of the invention may optionally comprise other active and inactive ingredients typically associated with cosmetic and personal care products, including, but not limited to, excipients, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfoliants, lubricants, fragrances, colorants, staining agents, depigmenting agents, hypopigmenting agents, preservatives, stabilizers, pharmaceutical agents, photostabilizing agents, and mixtures thereof. If present, the levels of such additional components should be judiciously selected so as not to adversely impact the ability of the emulsions to form superhydrophic films. Collectively, all such additional components should preferably comprise less than 5% by weight, more preferably less than 2% by weight, and more preferred still, less than 1% by weight of the total composition.

Cosmetic compositions according to the invention include, but are not limited to, color cosmetics, skin care products, hair care products, and personal care products. Color cosmetics include, for example, foundation and mascara. Skin care products include, but are not limited to, sunscreens, after-sun products, lotions, and creams. Additional applications include use in hair care products, insect repellents, deodorants, anti-perspirants, lipstick, ear canal product, baby wipes, baby creams or lotions, top coats to impart water-proofing or water-resistance to a previously applied cosmetic product, personal care product, hair care product, or first aid product. For example, the composition according to the invention could be applied as a top coat for a sunscreen or sunblock/insect repellant lotion previously applied to the skin to improve water-proofing or water-resistance. Alternatively, the composition could be applied as a top coat over a first aid product such as an antibiotic ointment or spray, bandage, or wound dressing.

In one embodiment, the composition is formulated as a sunscreen comprising hydrophobically modified (i.e., surface treated) titanium dioxide. The hydrophobically modified titanium dioxide may comprise at least about 50%, more typically at least about 75%, preferably at least about 85%, and more preferably at least about 95% of the total weight of the one or more particulate materials. In one embodiment, the particulate material will consist of or consist essentially of hydrophobically modified titanium dioxide. The sunscreens will optionally comprise one or more organic UVA and/or UVB filters (hydrophobic or hydrophilic), although the levels of hydrophilic organic sunscreens in the emulsions should not be so high as to adversely impact the ability to form a superhydrophobic surface and the aggregate amount of such organic sunscreens will preferably be below about 10% by weight, more preferably below about 5% by weight. The sunscreens according to the invention will exhibit improved water-resistance as compared to conventional emulsion-based sunscreens.

The present composition may have one or more active sunscreens. Such sunscreen actives may be organic or inorganic and water-soluble or oil-soluble. Such actives include those for UVA and UVB protection (290 to 400 nanometer solar radiation). Such sunscreen actives include, but are not limited to, one or more of the following: dibenzoylmethane, oxybenzone, sulisobenzone, dioxybenzone, menthyl anthranilate, para aminobenzoic acid (PABA), octyl methoxycinnamate, DEA methoxycinnamate, octocrylene, drometrizole trisiloxane, octyl salicylate, homomethyl salicylate, octyl dimethyl PABA, TEA salicylate, 4-methyl benzilidene camphor, octyl triazone, terephthalydiene dicamphor sulfonic acid, phenyl benzimidazole sulfonic acid, ethyl PABA, hydroxy methylphenyl benzotriazole, methylene bis-benzotriazoyltetramethylbutylphenol, bis-ethylhexyloxyphenol methoxyphenol triazine, titanium dioxide, zinc oxide, or any derivatives or any combinations thereof. Other useful sunscreen actives include those disclosed in U.S. Pat. No. 5,000,937, which is incorporated herein by reference. Preferred sunscreens include octylmethoxy cinnamate, octyl salicylate, octocrylene, avobenzone, benzophenone-3, and polysilicone-15 (Parsol slx).

In one embodiment, the compositions are applied to the skin, preferably the skin of the face. Such compositions may be formulated as a foundation, a blush, etc. In another embodiment, the compositions are provided as a water-resistant, transfer-resistant lip product (e.g., a lipstick or lip gloss). Color cosmetics will optionally comprise one or more colorants, including dyes, lakes, pigments, or combinations thereof.

In another embodiment, the compositions are applied to the hair and provide resistance against wetting. Thus, for example, the composition may be applied to the hair before swimming such that the hair does not become wet, or becomes only minimally wet, after submersion in water. By minimally wet is meant that the weight of the hair after submersion is increased by 100% or less, preferably by 50% or less, more preferably by 25% or less, and more preferred still by 10% or less as compared to the weight of the hair prior to submersion in water. Further, after one or two vigorous shakes of the hair, the hair will be essentially dry. By essentially dry is meant that the weight of the hair will be increased by less than about 5% or less than about 2.5% as compared to the weight of the hair before submersion. The foregoing may be tested using hair swatches treated with the inventive compositions. Likewise, the compositions may be applied to the hair of a pet, such as a dog, before swimming such that the pet is substantially dry immediately after swimming without the need for toweling off, etc., or to livestock so they are not wetted by snow, rain or mud.

Additional components may be incorporated as fillers or for various functional purposes as is customary in the cosmetic arts. However, while additional components consistent to formulate the above cosmetic compositions may be included, the inclusion of additional ingredients is limited to those ingredients which do not interfere with the formation of a superhydrophobic film.

EXAMPLES

Example 1

This Example provides an emulsion for imparting a superhydrophobic film on the hair. Emulsion formulations 1A, 1B, and 1C were prepared according to Table 1.

TABLE 1

| INCI name/description | 1A[9] | 1B | 1C |
|---|---|---|---|
| cyclopentasiloxane[1] | 60 | 50 | 60 |
| bis hydroxypropyldimethicone/SMDI copolymer and isododecane[2] | 5 | — | 2.5 |
| dimethicone and dimethiconol[3] | — | — | 2.5 |
| cyclopentasiloxane and acrylates/dimethicone copolymer[4] | — | 5 | — |
| Alumina and Trimethoxycaprylylsilane[5] | 5 | — | — |
| hydrophobic fumed silica[6] | — | 3.5 | 5 |
| iron oxide and triethoxycaprylylsilane[7] | — | 1.5 | — |
| peg/ppg-18/18 dimethicone and cyclopentasiloxane[8] | 10 | 10 | 10 |
| Alcohol SD 40B | 10 | — | 10 |
| Water | 10 | 30 | 10 |
| total | 100 | 100 | 100 |

[1]Cyclomethicone from Dow Corning;
[2]Silmer UR-5050 from Siltech;
[3]Q2-1403 fluid from Dow Corning;
[4]KP 545 Silicone Acrylate polymer from Shin-Etsu;
[5]Aeroxide Alu C 805 fumed Alumina from Degussa;
[6]Aeroxide LE 3 from Degussa;
[7]Iron Oxide Black NF 11S2 from Kobo;
[8]Dow Corning 5225C;
[9]All amounts given in weight percentages.

Emulsions 1A, 1B, and 1C were applied as a film to glass slides and volatiles were allowed to evaporate. The contact angles with a drop of water were measured to be 141.7 (1A), 145 (1B), and 143.3 (1C). In this and the following examples, the contact angles were measured using a Kruss prop Shape Analysis System DSA 10 MK2. The contact angle was calculated via the instrument software using the circle fit method. The water volume (i.e., drop size) was set to 5 µl.

Example 2

This example provides an emulsion based mascara for imparting a superhydrophobic film on the eyelashes. The emulsion was prepared according to the formulation provided in Table 2.

TABLE 2

| INCI name/description | Weight % |
| --- | --- |
| isododecane (IDD) | 50 |
| beeswax | 2.5 |
| candelilla wax | 2.5 |
| acrylates/stearyl acrylate/dimethicone methacrylate copolymer[1] | 9.5 |
| isododecane and acrylates/dimethicone copolymer[2] | 5 |
| glyceryl stearate | 1 |
| D&C black No. 2[3] | 1 |
| hydrophobic fumed silica[4] | 11 |
| iron oxide and triethoxycaprylylsilane[5] | 3 |
| peg/ppg-19/19 dimethicone and hydrogenated polyisobutene[6] | 2.5 |
| butylene glycol | 0.5 |
| sodium chloride | 0.5 |
| water | 11 |
| total | 100 |

[1]KP 561 was from Shin-Etsu;
[2]KP 550 from Shin Etsu;
[3]Carbon Black from LCW;
[4]Aeroxide LE 3 from Degussa;
[5]Iron Oxide Black NF11S2 from Kobo;
[6]Dow Corning BY 25-337.

A film was prepared by depositing the emulsion on a glass slide and permitting the volatiles to evaporate. The contact angle with a drop of water was measured to be 142.7±1.97.

Example 3

This example provides an emulsion based foundation for imparting a superhydrophobic film on the skin of the face. The emulsion was prepared according to the formulation provided in Table 3.

TABLE 3

| INCI name/description | Weight % |
| --- | --- |
| isododecane (IDD) | 25.78 |
| alumina and triethoxycaprylylsilane[1] | 3 |
| alumina and trimethoxycaprylylsilane[2] | 6 |
| isododecane and acrylates/dimethicone copolymer[3] | 11.02 |
| isododecane and ethylene/propylene/styrene copolymer and butylene/ethylene/styrene copolymer[4] | 15 |
| lauryl peg/ppg-18/18 methicone[5] | 0.5 |
| boron nitride | 4 |
| polymethyl methacrylate[6] | 5 |
| nylon-12 powder[7] | 2 |
| cellulose[8] | 5 |
| surface treated titanium dioxide[9] | 13.3 |
| titanium dioxide/triethoxycaprylylsilane[10] | 2 |
| iron oxide and triethoxycaprylylsilane[11] | q.s. to shade |
| red iron oxide and cetyl dimethicone[12] | q.s. to shade |
| yellow iron oxide and cetyl dimethicone[13] | q.s. to shade |
| water | 5 |
| butylene glycol | 1 |
| botanical extract[14] | 0.6 |
| total | 100 |

[1]Covalumine AS from Sensient;
[2]Aeroxide Alu C 805 from Degussa;
[3]KP550 from Shin-Etsu;
[4]Versagel MD 1600 from Penreco;
[5]Dow Corning 5200 formulation aid;
[6]PMMA spherical from Kobo;
[7]Orgasol nylon powder from Lipo;
[8]Cellulobead from Kobo;
[9]Tayca MT100SAS TiO2 AS treated from Tayca;
[10]TiO2 AS treated from Cardre;
[11]Black Iron Oxide NF 11S2 from Kobo;
[12]Red Iron Oxide from Ciba;
[13]Yellow Iron Oxide from Ciba;
[14]Sebustop from Barnet.

A film was prepared by depositing the emulsion on a glass slide and permitting the volatiles to evaporate. The contact angle with a drop of water was measured to be 146.8.

Example 4

This example provides an emulsion based sunscreen which imparts a superhydrophobic film on the skin. The emulsion was prepared according to the formulation provided in Table 4. Organic sunscreens, including those listed herein, or insect repellents, for example, DEET, IR3535, or Picaridin, may be added to this formulation as well.

TABLE 4

| INCI name/description | Weight % |
| --- | --- |
| Cyclopentasiloxane | 15 |
| Titanium dioxide and trimethoxycaprylylsilane[1] | 6 |
| Alumina and Trimethoxycaprylylsilane[2] | 6 |
| isododecane (IDD) | 15 |
| isododecane and acrylates/dimethicone copolymer[3] | 8 |
| peg/ppg-18/18 dimethicone and cyclopentasiloxane[4] | 7.5 |
| Dimethicone and dimethiconol[5] | 2.5 |
| water | 40 |
| total | 100 |

[1]Tegosun T 805 G from Degussa;
[2]Aeroxide Alu C 805 from Degussa;
[3]KP550 from Shin-Etsu;
[4]Dow Corning 5225C;
[5]Dow corning 1403 fluid.

The contact angle with water was measured as above and found to be 144.9.

Example 5

This example provides skin care emulsion which imparts a superhydrophobic film on the skin. The emulsion was prepared according to the formulation provided in Table 5.

TABLE 5

| INCI name/description | 5A[5] | 5B |
| --- | --- | --- |
| hydrophobic fumed silica[1] | 5.0 | 5.0 |
| disiloxane[2] | 41.0 | 58.0 |

TABLE 5-continued

| INCI name/description | 5A[5] | 5B |
|---|---|---|
| peg/ppg-19/19 dimethicone and hydrogenated polyisobutene[3] | 2.0 | 2.0 |
| bis hydroxypropyldimethicone/smdi copolymer and isododecane[4] | — | 5.0 |
| water | 52.0 | 30.0 |
| total | 100 | 100 |

[1]Aeroxide LE3 from Degussa;
[2]Silicone Fluid .65 cs from Dow Corning;
[3]Ts50-IP emulsifier from Dow Corning;
[4]Silmer UR-5050 from Siltech;
[5]All amounts given in weight percentages.

The contact angle with water was measured as above and found to be 140.6 for formula 5A and 143.7 for formula 5B.

When the above compositions were applied to skin or hair they rendered the skin and hair non-wettable, yet had favorable aesthetics.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims. All publications cited herein are incorporated by reference in their entirety.

The invention claimed is:

1. A method for providing a hydrophobic film on hair comprising
   (1) depositing on hair a composition in the form of a water-in-silicone emulsion, wherein said composition comprises:
      (i) a continuous silicone oil-phase comprising a volatile silicone;
      (ii) a discontinuous aqueous phase comprising water and ethanol;
      (iii) one or more emulsifiers comprising an organosiloxane polymer having alkoxylated side chains, said side chains comprising -(EO)m- and/or —(PO)n- groups, wherein the sum of n and m is about 50 or less, the side chains being terminated with hydrogen or lower alkyl groups, and wherein said one or more emulsifiers present in the composition have an HLB value below 8.5;
      (iv) one or more hydrophobic film formers;
      (v) one or more hydrophobic particulate materials having a median particle size between about 5 nm and about 1 mm; said one or more hydrophobic particulate materials comprising fumed alumina particles surface modified with alkyl silane moieties, the weight ratio of said one or more hydrophobic film formers to said one or more hydrophobic particulate materials being from about 1:5 to about 5:1; and said one or more hydrophobic film formers and said one or more hydrophobic particulate materials collectively comprising about 2% or more by weight of said water-in-oil emulsion; and
      (vi) optionally, a polyol, and optionally non-volatile water-dispersible or water-soluble constituents; and
   (2) allowing volatile constituents to evaporate,
   wherein the aggregate weight percentage of any of said non-volatile water-soluble or water-dispersible organic constituents, in said water-in-silicone emulsion, is less than 15%, based on the entire weight of the emulsion; and wherein hair on which said film has been deposited exhibits less than 25% weight gain following submersion in water.

2. The method according to claim 1, wherein the fumed alumina particles surface modified with alkyl silane moieties are the product of the reaction of fumed alumina with trimethoxycaprylylsilane or triethoxycaprylylsilane.

3. The method according to claim 1, wherein the weight ratio of said one or more hydrophobic film formers to said one or more hydrophobic particulate materials is from about 1:5 to about 2:1.

4. The method according to claim 1, wherein at least one of said one or more hydrophobic particulate materials has a median particle size between about 7 nm and about 40 nm.

5. The method according to claim 2, wherein at least one of said one or more hydrophobic particulate materials has a median particle size between about 7 nm and about 40 nm.

6. The method according to claim 1, wherein the aggregate weight percentage of any of said non-volatile water-soluble or water-dispersible organic constituents in said water-in-oil emulsion is less than 5%, and wherein the weight percentage of any polyols present is collectively below 1%.

7. The method according to claim 1, wherein said one or more hydrophobic film formers are selected from the group consisting of (alkyl)acrylates, polyurethanes, fluoropolymers, silicones, and copolymers thereof.

8. The method according to claim 7, wherein said one or more hydrophobic film formers comprise an acrylates/dimethicone copolymer.

9. The method according to claim 1, wherein the sum of n and m is 20 or less.

10. The method according to claim 1, wherein the sum of n and m is 10 or less.

11. The method according to claim 1, wherein said one or more emulsifiers is selected from the group consisting of dimethicone PEG 10/15 crosspolymer, dimethicone copolyol, cetyl dimethicone copolyol, PEG-15 lauryl dimethicone crosspolymer, laurylmethicone crosspolymer, PEG/PPG-18/18 dimethicone, PEG/PPG-19/19 dimethicone, cetyl PEG/PPG-10/1 dimethicone, PEG-12 dimethicone, lauryl PEG/PPG-18/18 methicone, PEG-12 dimethicone crosspolymer, PEG-10 dimethicone crosspolymer, and dimethicone PEG-10/15 crosspolymer.

12. The method according to claim 1, wherein said one or more emulsifiers is present in an amount from about 0.001 wt % to about 5 wt %, based on the total weight of the composition.

13. The method according to claim 11, wherein said one or more emulsifiers is present in an amount from about 0.001 wt % to about 5 wt %, based on the total weight of the composition.

14. The method according to claim 1 wherein said composition is free of pentylene glycol.

* * * * *